(12) United States Patent
Kiester

(10) Patent No.: US 8,343,192 B2
(45) Date of Patent: Jan. 1, 2013

(54) EXPANDABLE ROD SYSTEM TO TREAT SCOLIOSIS AND METHOD OF USING THE SAME

(75) Inventor: P. Douglas Kiester, Irvine, CA (US)

(73) Assignee: Ellipse Technologies, Inc., Irvine, CA (US)

( * ) Notice: Subject to any disclaimer, the term of this patent is extended or adjusted under 35 U.S.C. 154(b) by 538 days.

(21) Appl. No.: 12/421,569

(22) Filed: Apr. 9, 2009

(65) Prior Publication Data

US 2009/0204154 A1    Aug. 13, 2009

Related U.S. Application Data

(62) Division of application No. 11/172,678, filed on Jun. 30, 2005, now Pat. No. 7,955,357.

(60) Provisional application No. 60/584,961, filed on Jul. 2, 2004.

(51) Int. Cl.
*A61B 17/88* (2006.01)
(52) U.S. Cl. ......... 606/279; 606/246; 606/251; 606/256
(58) Field of Classification Search .................... 606/63, 606/68, 258–260, 266, 279
See application file for complete search history.

(56) References Cited

U.S. PATENT DOCUMENTS

| | | |
|---|---|---|
| 2,702,031 A | 2/1955 | Wenger |
| 3,810,259 A | 5/1974 | Summers |
| 3,976,060 A | 8/1976 | Hildebrandt et al. |
| 4,078,559 A * | 3/1978 | Nissinen .................. 606/258 |
| 4,448,191 A | 5/1984 | Rodnyansky et al. |
| 4,658,809 A | 4/1987 | Ulrich |
| 4,854,304 A | 8/1989 | Zielke |
| 4,931,055 A * | 6/1990 | Bumpus et al. .................. 606/60 |
| 4,957,495 A * | 9/1990 | Kluger ............................. 606/58 |
| 5,010,879 A | 4/1991 | Moriya et al. |

(Continued)

FOREIGN PATENT DOCUMENTS

DE        8515687        12/1985

(Continued)

OTHER PUBLICATIONS

Abe, J. Nagata, K., Ariyoshi, M., Inoue, A., "Experimental External Fixation Combined with Pecutaneous Discectomy in the Management of Scoliosis", Spine, 1999, vol. 24, No. 7, pp. 646-653, Lippincott Co., Philadelphia, U.S.A.

(Continued)

*Primary Examiner* — Alvin Stewart
*Assistant Examiner* — Stuart S Bray
(74) *Attorney, Agent, or Firm* — Vista IP Law Group LLP

(57) ABSTRACT

Correction of a scoliotic curve in a spine comprises the steps of implanting an expanding rod isolated completely under the skin and attached to selected portions of the scoliotic curve of the spine at opposing ends of the rod; and producing a controlled force by means of expansion of the rod over at an extended time period under external control until a desire spinal curve is obtained. An incremental force is generated to stretch the scoliotic curve of the spine between the selected portions where attachment of the rod is defined. The controlled force is provided steadily for at least one month or alternatively 1-3 months. Multiple rods may be employed each associated with a different scoliotic curve of the spine or a different portion of the scoliotic curve.

23 Claims, 6 Drawing Sheets

U.S. PATENT DOCUMENTS

| | | | |
|---|---|---|---|
| 5,030,235 | A | 7/1991 | Campbell, Jr. |
| 5,092,889 | A | 3/1992 | Campbell, Jr. |
| 5,133,716 | A * | 7/1992 | Plaza .......................... 606/250 |
| 5,261,908 | A | 11/1993 | Campbell, Jr. |
| 5,263,955 | A | 11/1993 | Baumgart et al. |
| 5,290,289 | A | 3/1994 | Sanders et al. |
| 5,466,261 | A | 11/1995 | Richelsoph |
| 5,575,790 | A * | 11/1996 | Chen et al. .................... 606/60 |
| 5,626,579 | A | 5/1997 | Muschler et al. |
| 5,632,744 | A | 5/1997 | Campbell, Jr. |
| 5,672,175 | A | 9/1997 | Martin |
| 5,704,939 | A | 1/1998 | Justin |
| 5,720,746 | A | 2/1998 | Soubeiran |
| 5,800,434 | A | 9/1998 | Campbell, Jr. |
| 5,810,815 | A | 9/1998 | Morales |
| 5,961,553 | A | 10/1999 | Coty et al. |
| 6,033,412 | A | 3/2000 | Losken et al. |
| 6,106,525 | A | 8/2000 | Sachse |
| 6,126,660 | A * | 10/2000 | Dietz .............................. 606/90 |
| 6,200,317 | B1 | 3/2001 | Aalsma et al. |
| 6,336,929 | B1 | 1/2002 | Justin |
| 6,343,568 | B1 | 2/2002 | McClasky |
| 6,358,283 | B1 | 3/2002 | Hogfors et al. |
| 6,417,750 | B1 | 7/2002 | Sohn |
| 6,616,669 | B2 | 9/2003 | Ogilvie et al. |
| 6,765,330 | B2 | 7/2004 | Baur |
| 6,796,984 | B2 | 9/2004 | Soubeiran |
| 6,835,207 | B2 | 12/2004 | Zacouto et al. |
| 6,849,076 | B2 | 2/2005 | Blunn et al. |
| 6,918,910 | B2 | 7/2005 | Smith et al. |
| 7,011,658 | B2 * | 3/2006 | Young ........................... 606/258 |
| 7,029,472 | B1 * | 4/2006 | Fortin ............................. 606/60 |
| 7,135,022 | B2 * | 11/2006 | Kosashvili et al. ............ 606/63 |
| 7,481,841 | B2 * | 1/2009 | Hazebrouck et al. ....... 623/18.12 |
| 7,942,908 | B2 * | 5/2011 | Sacher et al. ................. 606/258 |
| 2002/0138077 | A1 * | 9/2002 | Ferree ............................. 606/61 |
| 2003/0220643 | A1 | 11/2003 | Ferree |
| 2004/0030395 | A1 * | 2/2004 | Blunn et al. ............... 623/18.12 |
| 2004/0193266 | A1 | 9/2004 | Meyer |
| 2004/0236329 | A1 | 11/2004 | Panjabi |
| 2005/0055025 | A1 | 3/2005 | Zacouto et al. |
| 2005/0113927 | A1 | 5/2005 | Malek |
| 2005/0234448 | A1 | 10/2005 | McCarthy |
| 2005/0246034 | A1 | 11/2005 | Soubeiran |
| 2005/0251109 | A1 | 11/2005 | Soubeiran |
| 2005/0261779 | A1 | 11/2005 | Meyer |
| 2006/0004459 | A1 | 1/2006 | Hazebrouck et al. |
| 2006/0009767 | A1 | 1/2006 | Kiester |
| 2006/0036323 | A1 | 2/2006 | Carl et al. |
| 2006/0036324 | A1 | 2/2006 | Sachs et al. |
| 2006/0047282 | A1 | 3/2006 | Gordon |
| 2006/0052782 | A1 | 3/2006 | Morgan et al. |
| 2006/0058792 | A1 | 3/2006 | Hynes |
| 2006/0069447 | A1 | 3/2006 | DiSilvestro et al. |
| 2006/0074448 | A1 | 4/2006 | Harrison et al. |
| 2006/0079897 | A1 | 4/2006 | Harrison et al. |
| 2006/0136062 | A1 | 6/2006 | DiNello et al. |
| 2006/0155279 | A1 | 7/2006 | Ogilvie |
| 2006/0195087 | A1 | 8/2006 | Sacher et al. |
| 2006/0195088 | A1 * | 8/2006 | Sacher et al. ................... 606/61 |
| 2006/0271107 | A1 | 11/2006 | Harrison et al. |
| 2007/0010887 | A1 | 1/2007 | Williams et al. |
| 2007/0050030 | A1 | 3/2007 | Kim |
| 2007/0055125 | A1 * | 3/2007 | Anderson et al. ............. 600/407 |
| 2007/0179493 | A1 | 8/2007 | Kim |
| 2007/0213751 | A1 | 9/2007 | Scirica et al. |
| 2007/0213812 | A1 * | 9/2007 | Webler et al. ................ 623/2.11 |
| 2007/0233098 | A1 | 10/2007 | Mastrorio et al. |
| 2007/0239161 | A1 | 10/2007 | Giger et al. |
| 2007/0255088 | A1 | 11/2007 | Jacobson et al. |
| 2007/0270803 | A1 | 11/2007 | Giger et al. |
| 2007/0276368 | A1 | 11/2007 | Trieu et al. |
| 2007/0276369 | A1 | 11/2007 | Allard et al. |
| 2007/0276378 | A1 | 11/2007 | Harrison et al. |
| 2007/0288024 | A1 | 12/2007 | Gollogly |
| 2008/0027436 | A1 | 1/2008 | Cournoyer et al. |
| 2008/0033436 | A1 | 2/2008 | Song et al. |
| 2008/0048855 | A1 | 2/2008 | Berger |
| 2009/0030462 | A1 | 1/2009 | Butterman |
| 2010/0106192 | A1 * | 4/2010 | Barry ............................ 606/258 |
| 2012/0022597 | A1 * | 1/2012 | Gephart et al. ............... 606/279 |
| 2012/0089191 | A1 * | 4/2012 | Altarac et al. ................. 606/279 |

FOREIGN PATENT DOCUMENTS

| | | |
|---|---|---|
| DE | 102005045070 A1 | 4/2007 |
| FR | 2900563 A1 | 11/2007 |
| FR | 2901991 A1 | 12/2007 |
| WO | WO 99/51160 A1 | 10/1999 |
| WO | WO 2004/019796 A1 | 3/2004 |
| WO | WO 2006/090380 A2 | 8/2006 |
| WO | WO 2007/015239 A2 | 2/2007 |
| WO | WO 2007/025191 A1 | 3/2007 |
| WO | WO 2007/118179 A2 | 10/2007 |
| WO | WO 2007/144489 A2 | 12/2007 |
| WO | WO 2008/003952 A1 | 1/2008 |
| WO | WO 2008/040880 A2 | 4/2008 |

OTHER PUBLICATIONS

Buchowski, J., Bhatnagar, R., Skaggs, D., Sponseller, P., "Temporary Internal Distraction as an Aid to Correction of Severe Scoliosis", Journal of Bone and Joint Surgery American Edition, 2006, vol. 88A, No. 9, pp. 2035-2041, Journal of Bone and Joint Surgery, Boston, U.S.A.

Buchowski, J., Skaggs, D., Sponseller, P., "Temporary Internal Distraction as an Aid to Correction of Severe Scoliosis. Surgical Technique", Journal of Bone and Joint Surgery American Edition, 2007, vol. 89A No. Supp 2 (Pt. 2), pp. 297-309, Journal of Bone and Joint Surgery, Boston, U.S.A.

Burke, J. "Design of a Minimally Invasive Non Fusion Device for the Surgical Management of Scoliosis in the Skeletally Immature", Studies in Health Technology and Informatics, 2006, vol. 123, pp. 378-384, IOS Press, Amsterdam, The Netherlands.

Cole, J., Paley, D., Dahl, M., "Operative Technique. ISKD. Intramedullary Skeletal Kinetic Distractor. Tibial Surgical Technique" IS-0508(A)-OPT-US © Orthofix Inc. Nov. 2005.

Daniels, A., Gemperline, P., Grahn, A., Dunn, H., "A New Method for Continuous Intraoperative Measurement of Harrington Rod Loading Patterns", Annals of Biomedical Engineering, 1984, vol. 12, No. 3, pp. 233-246, Dordrecht Kluwer Academic/Plenum Publishers, New York, U.S.A.

Edelan, H., Eriksson, G., Dahlberg, E., "Instrument for distraction by limited surgery in scoliosis treatment", Journal of Biomedical Engineering, 1981, vol. 3, No. 2, pp. 143-146, Butterfield Scientific Limited, Guilford, England.

Ember, T., Noordeen, H., "Distraction forces required during growth rod lengthening", Journal of Bone and Joint Surgery British Edition, 2006, vol. 88B, No. Supp II, p. 229, Churchill Livingstone, London, England.

Gao et al., CHD7 Gene Polymorphisms Are Associated with Susceptibility to Idiopathic Scoliosis, American Journal of Human Genetics, vol. 80, pp. 957-965 (May 2007).

Gebhart, M., Neel, M., Soubeiran, A., Dubousset, J., "Early clinical experience with a custom made growing endoprothesis in children with malignant bone tumors of the lower extremity actioned by an external permanent magnet: the Phenix M system", International Society of Limb Salvage 14th International Symposium on Limb Salvage, Sep. 13, 2007, Hamburg, Germany.

Gillespie, R., O'Brien, J., "Harrington Instrumentation without Fusion", The Journal of Bone and Joint Surgery British Edition, 1981, vol. 63B, No. 3, p. 461, Churchill Livingstone, London, England.

Grass, P., Soto, A., Araya, H., "Intermittent Distracting Rod for Correction of High Neurologic Risk Congenital Scoliosis", Spine, 1997, vol. 22, No. 16, pp. 1922-1927, Lippincott Co., Philadelphia, U.S.A.

Grimer, R., Chotel, F., Abudu, S., Tillman, R., Carter, S., "Non-invasive extendable endoprothesis for children—expensive but worth it", International Society of Limb Salvage 14th International Symposium on Limb Salvage, Sep. 13, 2007, Hamburg, Germany.

Gupta, A., Meswania, J., Pollock, R., Cannon, S., Briggs, T., Taylor, S., Blunn, G., "Non-Invasive Distal Femoral Expandable Endoprosthesis for Limb-Salvage Surgery in Paediatric Tumours", The Journal of Bone and Joint Surgery British Edition, 2006, vol. 88-B, No. 5, pp. 649-654, Churchill Livingstone, London, England.

Hankemeier, S., Gösling, T., Pape, H., Wiebking, U., Krettek, C., "Limb Lengthening with the Intramedullary Skeletal Kinetic Distractor (ISKD)", Operative Orthopädie und Traumatologie, 2005, vol. 17, No. 1, pp. 79-101, Urban & Vogel, Munich, Germany.

Harrington, P., "Treatment of Scoliosis: Correction and Internal Fixation by Spine Instrumentation", The Journal of Bone and Joint Surgery American Edition, 1962, vol. 44A, No. 4, pp. 591-610, Journal of Bone and Joint Surgery, Boston, U.S.A.

Klemme, W., Denis, F., Winter, R., Lonstein, J., Koop, S., "Spinal Instrumentation without Fusion for Progressive Scoliosis in Young Children", Journal of Pediatric Orthopedics. 1997, vol. 17, No. 6, pp. 734-742, Raven Press, New York, U.S.A.

Lonner, B., "Emerging minimally invasive technologies for the management of scoliosis", Orthopedic Clinics of North America, 2007; vol. 38, No. 3, pp. 431-440, Saunders, Philadelphia, U.S.A.

Mineiro, J., Weinstein, S., "Subcutaneous Rodding for Progressive Spinal Curvatures: Early Results", Journal of Pediatric Orthopedics, 2002, vol. 22, No. 3, pp. 290-295, Raven Press, New York, U.S.A.

Moe, J., Kharrat, K., Winter, R., Cummine, J., "Harrington Instrumentation without Fusion Plus External Orthotic Support for the Treatment of Difficult Curvature Problems in Young Children", Clinical Orthopaedics and Related Research, 1984, No. 185. pp. 35-45, Lippincott Co., Philadelphia, U.S.A.

Nachemson, A., Elfstrom, G., "Intravital Wireless Telemetry of Axial Forces in Harrington Distraction Rods in Patients with Idiopathic Scoliosis", The Journal of Bone and Joint Surgery American Edition, 1971, vol. 53A, No. 3, pp. 445-465, Journal of Bone and Joint Surgery, Boston, U.S.A.

Nachlas, I., Borden, J., "The cure of experimental scoliosis by directed growth control". The Journal of Bone and Joint Surgery American Edition, 1951, vol. 33, No. A:1, pp. 24-34, Journal of Bone and Joint Surgery, Boston, U.S.A.

Newton, P., "Fusionless Scoliosis Correction by Anterolateral Tethering . . . Can it Work?", 39th Annual Scoliosis Research Society Meeting, Sep. 6, 2004, Buenos Aires, Argentina (transcript and slides supplied).

Rathjen, K, Wood, M., McClung, A., Vest, Z., "Clinical and Radiographic Results after Implant Removal in Idiopathic Scoliosis", Spine, 2007, vol. 32, No. 20, pp. 2184-2188, Lippincott Co., Philadelphia, U.S.A.

Reyes-Sanchez, A., Rosales, L, Miramontes, V., "External Fixation for Dynamic Correction of Severe Scoliosis", The Spine Journal, 2005, vol. 5, No. 4, pp. 418-426, Elsevier Science Inc., New York, U.S.A.

Rinsky, L., Gamble, J., Bleck, E., "Segmental Instrumentation Without fusion in Children with Progressive Scoliosis", Journal of Pediatric Orthopedics, 1985, vol. 5, No. 6, pp. 687-690, Raven Press, New York, U.S.A.

Schmerling, M., Wilkov, M., Sanders, A., "Using the Shape Recovery of Nitinol in the Harrington Rod Treatment of Scoliosis", Journal of Biomedical Materials Research, 1976, vol. 10, No. 6, pp. 879-892, Wiley, Hoboken, U.S.A.

Sharke, P., "The Machinery of Life", Mechanical Engineering Magazine, Feb. 2004, Printed from Internet site Oct. 24, 2007 http://www.memagazine.org/contents/current/features/moflife/moflife.html.

Smith J., "The Use of Growth-Sparing Instrumentation in Pediatric Spinal Deformity", Orthopedic Clinics of North America, 2007, vol. 38, No. 4, pp. 547-552, Saunders, Philadelphia, U.S.A.

Soubeiran, A., Gebhart, M., Miladi, L., Griffet, J., Neel, M., Dubousset, J., "The Phenix M System. A Mechanical Fully Implanted Lengthening Device Externally Controllable Through the Skin with a Palm Size Permanent Magnet; Applications to Pediatric Orthopaedics", 6th European Research Conference in Pediatric Orthopaedics, Oct. 6, 2006, Toulouse, France.

Soubeiran, A., Gebhart, M., Miladi, L., Griffet, J., Neel, M., Dubousset, J., "The Phenix M system, a fully implanted non-invasive lengthening device externally controllable through the skin with a palm size permanent magnet. Applications in limb salvage." International Society of Limb Salvage 14th International Symposium on Limb Salvage, Sep. 13, 2007, Hamburg, Germany.

Takaso, M., Moriya, H., Kitahara, H., Minami, S., Takahashi, K., Isobe, K., Yamagata, M., Otsuka, Y., Nakata, Y., Inoue, M., "New remote-controlled growing-rod spinal instrumentation possibly applicable for scoliosis in young children", Journal of Orthopaedic Science, 1998, vol. 3, No. 6, pp. 336-340, Springer-Verlag, Tokyo, Japan.

Thompson, G., Akbarnia, B., Campbell, R., "Growing Rod Techniques in Early-Onset Scoliosis", Journal of Pediatric Orthopedics, 2007, vol. 27, No. 3, pp. 354-361, Raven Press, New York, U.S.A.

Thompson, G., Lenke, L., Akbarnia, B., McCarthy, R., Campbell, Jr., R., "Early Onset Scoliosis: Future Directions", 2007, Journal of Bone and Joint Surgery American Edition, vol. 89A, No. Supp 1, pp. 163-166, Journal of Bone and Joint Surgery, Boston, U.S.A.

Trias, A., Bourassa, P., Massoud, M., "Dynamic Loads Experienced in Correction of Idiopathic Scoliosis Using Two Types of Harrington Rods", Spine, 1979, vol. 4, No. 3, pp. 228-235, Lippincott Co., Philadelphia, U.S.A.

Verkerke, G., Koops, H., Veth, R., Oldhoff, J., Nielsen, H., vanden Kroonenberg, H., Grootenboer, H., van Krieken, F., "Design of a Lengthening Element for a Modular Femur Endoprosthetic System", Proceedings of the Institution of Mechanical Engineers Part H: Journal of Engineering in Medicine, 1989, vol. 203, No. 2, pp. 97-102, Mechanical Engineering Publications, London, England.

Verkerke, G., Koops, H., Veth, R., van den Kroonenberg, H., Grootenboer, H., Nielsen, H., Oldhoff, J., Postma, A., "An Extendable Modular Endoprosthetic System for Bone Tumour Management in the Leg", Journal of Biomedical Engineering, 1990, vol. 12, No. 2, pp. 91-96, Butterfield Scientific Limited, Guilford, England.

Verkerke, G., Koops, H., Veth, R., Grootenboer, H., De Boer, L., Oldhoff, J., Postma, A. "Development and Test of an Extendable Endoprosthesis for Bone Reconstruction in the Leg", The International Journal of Artificial Organs, 1994, vol. 17, No. 3, pp. 155-162, Wichtig Editore, Milan, Italy.

Wenger, H., "Spine Jack Operation in the Correction of Scoliotic Deformity", Archives of Surgery, 1961, vol. 83, pp. 123-132 (901-910), American Medical Association, Chicago, U.S.A.

White, A., Panjabi, M., "The Clinical Biomechanics of Scoliosis", Clinical Orthopaedics and Related Research, 1976, No. 118, pp. 100-112, Lippincott Co., Philadelphia, U.S.A.

Tello C., "Harrington Instrumentation without Arthrodesis and Consecutive Distraction Program for Young Children with Sever Spinal Deformities: Experience and Technical Details", Orthopedic Clinics of North America, vol. 25, No. 2 1994. pp. 333-351. (19 pages).

Guichet, J., Deromedis, B., Donnan, L., Peretti, G., Lascombes, P., Bado,F., "Gradual Femoral Lengthening with the Albizzia Intramedullary Nail", Journal of Bone and Joint Surgery American Edition, 2003, vol. 85, pp. 838-848. (12 pages).

Marco Teli, M.D. et al. Measurement of Forces Generated During Distraction of Growing Rods. Marco Teli, J. Child Orthop (2007) 1:257-258.

Hazem Elsebaie M.D., Single Growing Rods (Review of 21 cases). Changing the Foundations: Does it affect the Results?, J Child Orthop. (2007) 1:258.

* cited by examiner

EXPANDABLE ROD SYSTEM TO TREAT SCOLIOSIS AND METHOD OF USING THE SAME

RELATED APPLICATIONS

The present application is a divisional of U.S. patent application Ser. No. 11/172,678 filed on Jun. 30, 2005, which itself claims priority to U.S. Provisional Patent Application Ser. No. 60/584,961, filed on Jul. 2, 2004, both of which are incorporated herein by reference and to which priority is claimed pursuant to 35 USC 119 and 120.

BACKGROUND OF THE INVENTION

1. Field of the Invention

The invention relates to the field of medical devices for treating scoliosis and methods of treatment using such medical devices, or methods of using such devices.

2. Description of the Prior Art

Adolescent (also called idiopathic) scoliosis is believed to be the direct result of a tight ligamentum flavum during rapid growth. The ligamentum flavum is a strong discontinuous (or segmental) ligament full of elastic fibers (which gives it its yellow color) that runs along the posterior aspect of the spinal canal. The posterior aspect of the dura, at any given spinal level, touches lamina for one third of its length, and ligamentum for the other two thirds. In the lumbar spine it acts as the center of rotation (and maybe the center of rotation for the thoracic as well, which would help explain the limited rotation available in the thoracic spine).

If indeed scoliosis is the result of a tight ligamentum flavum, then correction of scoliosis should be achievable by mechanical stretching. Rapid correction of a scoliotic curve is now possible because great force through multiple points of solid fixation are now available. These methods still, however, are described as steps toward inserting instrumentation for a fusion of vertebrae. A slower and steady stretch over time, would be much less violent, and would allow the use of much less force and fewer points of fixation.

What is needed is some kind of device and mechanics to perform the needed mechanical stretching.

BRIEF SUMMARY OF THE INVENTION

The illustrated embodiment of the invention includes a method for correction of a scoliotic curve in a spine comprising the steps of implanting an expanding rod isolated completely under the skin and attached to selected portions of the scoliotic curve of the spine at opposing ends of the rod; and producing a controlled force by means of expansion of the rod over at an extended time period under external control until a desire spinal curve is obtained.

The step of producing a controlled force comprises the step of generating an incremental force to stretch the scoliotic curve of the spine between the selected portions where attachment of the rod is defined. The step of generating an incremental force to stretch the scoliotic curve of the spine comprises the step of generating a force using a curved rod in a direction tending to align with the spine at the selected portions where attachment of the rod is defined.

The step of implanting the expanding rod comprises implanting the expanding rod posteriorly to the spine.

The step of producing a controlled force by means of expansion of the rod over at an extended time period comprises the step of producing the controlled force at a predetermined level over time without any combination with fusion of vertebrae.

The step of producing the controlled force by means of expansion of the rod over at an extended time period comprises producing the controlled force steadily for at least one month or alternatively 1-3 months.

The step of producing the controlled force by means of expansion of the rod over at an extended time period comprises the step of producing the controlled force steadily for such period of time as is sufficient to stretch the ligamentum flavum of the spine enough to allow the spine to straighten.

The invention further contemplates repeating the steps of implanting an expanding rod with multiple rods, where each rod is associated with a different scoliotic curve of the spine or a different portion of the scoliotic curve of the spine, and separately producing a controlled force by means of expansion of each corresponding rod over at a corresponding extended time period.

The step of producing the controlled force by means of expansion of the rod comprises the step of producing the controlled force by means of a ratcheted longitudinal extension of the rod powered by an energy sources biologically isolated from the rod by a skin barrier.

The invention also comprises an apparatus used for performing each of the above embodiments of the illustrated method. The invention thus includes among other embodiments a kit of a plurality of expanding rods with multiple rods, each rod being associated with a different scoliotic curve of the spine or a different portion of the scoliotic curve of the spine and separately producing a controlled force by means of expansion of each corresponding rod over at a corresponding extended time period.

The means for producing the controlled force by means of expansion of the rod comprises means for producing the controlled force by a ratcheted longitudinal extension of the rod powered by an energy sources biologically isolated from the rod by a skin barrier.

Stated in an alternative form, the invention includes embodiments where the invention is an apparatus for correction of a scoliotic curve in a spine comprising an expanding rod isolated completely under the skin; attachment screws to couple the rod to the spine at opposing ends of the rod; and a source of controlled force coupled to the rod to longitudinal extend the rod over an extended defined period of time under external control until a desire spinal curve is obtained.

The rod comprises a pair of telescopically coupled sleeves; and means to prevent relative rotation of the sleeves. The apparatus is combined with an external source of power, and in one embodiment the source of the controlled force comprises a torsion spring coupled to a second one of the pair of sleeves, a torsion motor coupled to the spring for torsioning the torsion spring, a power pick up electrically coupled to the torsion motor for powering the motor from the external source of power, a ratchet and a screw drive coupled to the ratchet at one end and to a first one of the pair of sleeves at an opposing end, so that a force applied to the screw drive from the torsion motor to the first one of the pair of sleeves over time longitudinally expands the collective length of the pair of sleeves. In the illustrated embodiment the torsion motor comprises a muscle wire.

More generally, where the invention is characterized as a combination of an expanding rod, attachment screws, a source of controlled force, and a ratchet, where the source of controlled force produces a force over a defined period of time, which force is continually maintained to some degree by the ratchet after initial generation by the source until the spine to which the force is steadily applied straightens at least to a partial degree.

While the apparatus and method has or will be described for the sake of grammatical fluidity with functional explanations, it is to be expressly understood that the claims, unless expressly formulated under 35 USC 112, are not to be construed as necessarily limited in any way by the construction of "means" or "steps" limitations, but are to be accorded the full scope of the meaning and equivalents of the definition provided by the claims under the judicial doctrine of equivalents, and in the case where the claims are expressly formulated under 35 USC 112 are to be accorded full statutory equivalents under 35 USC 112. The invention can be better visualized by turning now to the following drawings wherein like elements are referenced by like numerals.

Figure 1:
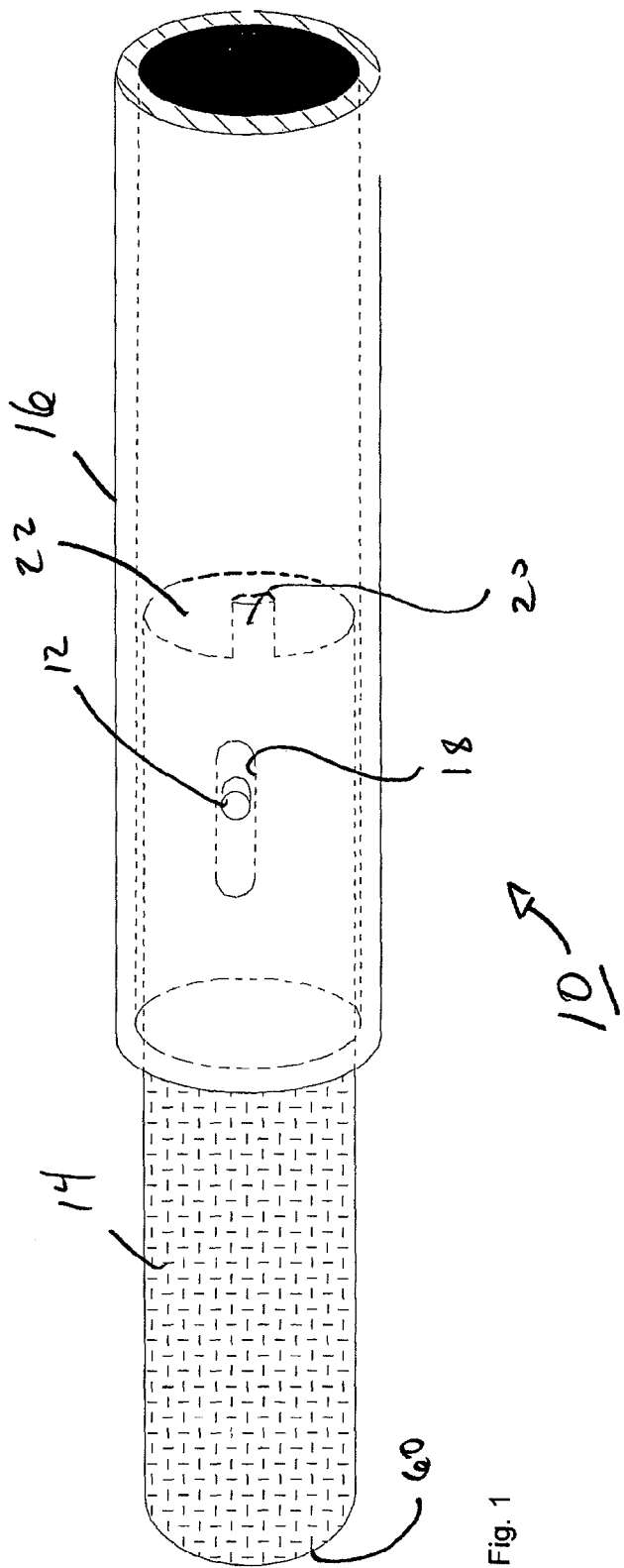
FIG. 1 is a side perspective view of a telescoping rod of the invention showing the telescopic sleeves.

The invention and its various embodiments can now be better understood by turning to the following detailed description of the preferred embodiments which are presented as illustrated examples of the invention defined in the claims. It is expressly understood that the invention as defined by the claims may be broader than the illustrated embodiments described below.

DETAILED DESCRIPTION OF THE PREFERRED EMBODIMENTS

The invention comprises a rod, generally denoted by reference numeral 10, for the treatment of scoliosis by slow stretching of selected biological tissues, for example, a selected portion of the spine, which is implantable into the body and is under external control. The invention allows for surgical treatment of the spine without fusion of any of the vertebrae, and can be used not only for scoliosis, but also in pediatric orthopedics such as for leg or limb lengthening.

For the purposes of the illustrated disclosure, it is assumed that adolescent (also called idiopathic) scoliosis is the direct result of a tight ligamentum flavum during rapid growth. The evidence for this assumption is impressive and overwhelming. The second assumption made in the illustrated disclosure for the sake of simplicity is that we are treating a simple, single curve, although the indications and complexities of extending the use of the invention to more complex curves is explicitly within the scope of the invention. Where multiple rods 10 are implanted each rod 10 may be fixed across a different scoliotic curve where multiple scoliotic curves exist, or may be fixed across different portions of a single scoliotic curve. In such a case, each one of the multiple rods can be separately controlled to produce the needed straightening force or expansion.

The proposed device comprises an expanding or telescopic rod 10 as shown in side perspective view in FIG. 1. As described below, the opposing ends of rod 10 will be fixed to selected positions on the spine using conventional surgical screws. The rod 10 must produce a controlled force, slowly over time, under precise external control, and be isolated or implanted completely under the skin and protected by the natural barrier, which the skin provides. Rod 10 also needs to be small, powerful, simple enough to be readily manufactured, immune to accidental activation, and biologically inert. Rod 10 of the illustrated embodiment meets each and all of these criteria.

The rod 10 can be as small as ½" (2.54 cm) in diameter and typically can be made much smaller, subject only material limitations arising from the strength of the rod 10 itself. Rod 10 is can be made from any bioengineered or biological inert material desired, and in the illustrated embodiment is fabricated from metal, such as surgical quality stainless steel. Rod 10 is comprised of an inner hollow cylindrical sleeve 14 telescopically disposed in outer, hollow cylindrical sleeve 16. The outer diameter of cylindrical sleeve 14 is chosen to telescopically slide without binding in the inner diameter of cylindrical sleeve 16 along their common longitudinal axes. A pin 12 is fixed to cylindrical sleeve 14 and extends radially therefrom through a longitudinal slot 18 defined through the wall of cylindrical sleeve 16 to stop rotation of cylindrical sleeve 14 relative to cylindrical sleeve 16 while allowing free relative longitudinal movement of cylindrical sleeve 14 relative to cylindrical sleeve 16 at least to the extent of the length of slot 18. Sleeves 14 and 16 are shown as circular cylinders in the illustrated embodiment, but pin 12 may be removed and elliptically or other prismatic shapes may be used in place of a cylindrical shape, which would equivalently stop or limit their relative rotation to each other. Therefore, the hollow outer sleeve 16 and inner sleeve 14 are configured to limit rotational movement between the hollow outer sleeve 16 and inner sleeve 14. When in the specification the term, "sleeve" is used without modification, it should be understood to have a general prismatic shape.

Figure 2:
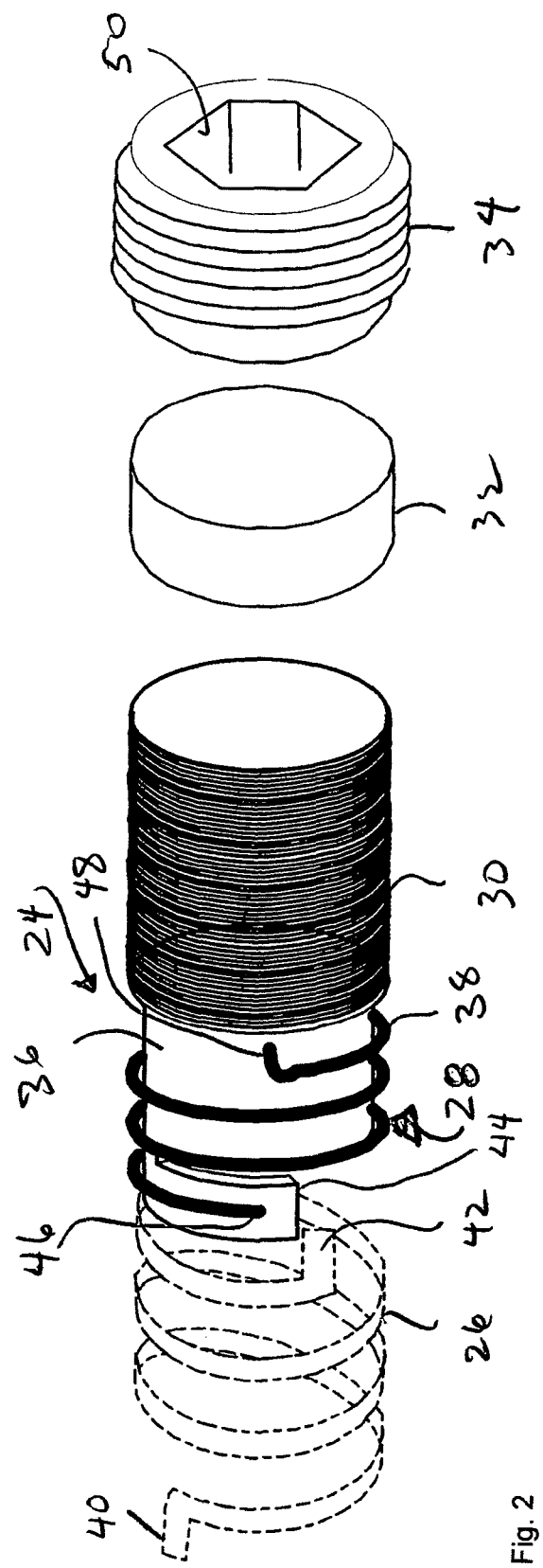
FIG. 2 is a side perspective view of a drive unit of the illustrated embodiment of the invention included in the rod of FIG. 1.
Figure 2A:
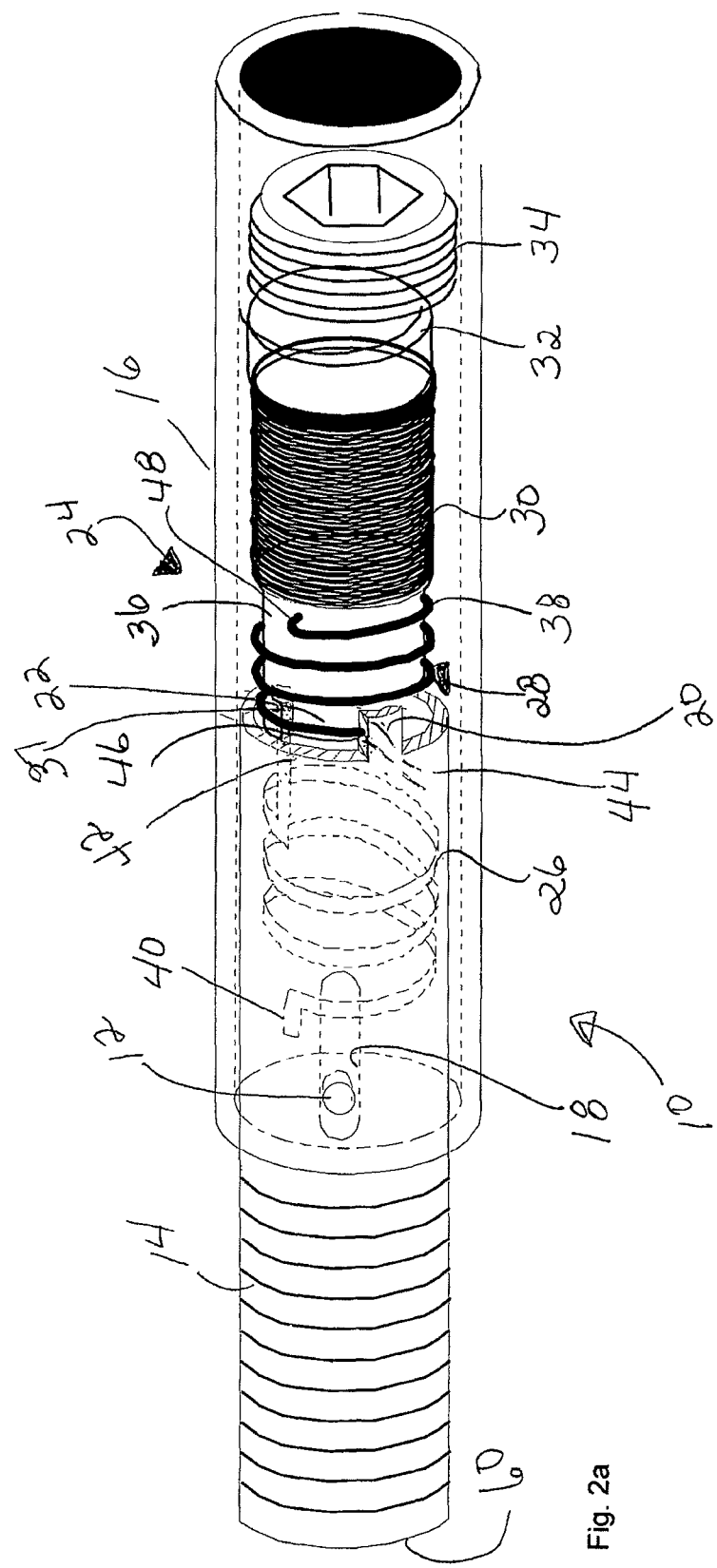
FIG. 2a is a side perspective transparent view of the invention as depicted in FIGS. 1 and 2 shown in assembled form.

The larger cylindrical sleeve 16 is internally threaded. The small longitudinally extending post 20 on the right end 22 of the smaller cylindrical sleeve 14 as seen in FIG. 1 is where the drive unit, generally denoted by reference numeral 24, attaches as described below. Drive unit 24 as shown in the side perspective view of FIG. 2 is housed or disposed inside the cylindrical sleeve 16 with the left end 40 of a torsion spring 26 disposed within and affixed to sleeve 14 as shown in FIG. 2a. The opposing end 42 of torsion spring 26 is coupled to or bears against a segment end 44 of shell 36. Shell 36 is disposed in sleeve 16 as shown in FIG. 2a and rotates within the end of sleeve 14, but is held by a stop(s) 37 from telescopically sliding into sleeve 14. Shell 36 is thus longitudinally fixed relative to sleeve 14, but is free to rotate relative to sleeve 14 at least through a defined angular range. Thus, as shell 36 is rotated as described below, torsion spring 26 which has on end connected to sleeve 14 and the other end to shell 36 will wind up or down depending on the sense of rotation of shell 36.

FIG. 2 shows the drive unit in exploded view which is comprised of spring 26, motor 28, pickup coil 30, ratchet 32 and screw drive 34. These elements represent the simplest configuration for the drive unit 24, although it must be understood that any drive unit now known or later devised capable of providing the same or similar force as the illustrated drive unit 24 can be equivalently substituted without departing from the illustrated embodiment of the invention. Because of energy transfer considerations relating to coil 30 and wire 38, additional electronic or electrical components may be required as discussed below.

The motor 28 comprises a muscle wire 38 wound onto a cylindrical shell 36. Muscle wire 38 is well known to the art and is also called nitinol wire. When current is passed through the wire 38, it heats and contracts. Wire 38 is electrically connected to or in circuit with coil 30 in which a current is inductively generated. One end 48 of wire 38 is coupled or connected to shell 36. The opposing end 46 of wire 38 is coupled or connected to sleeve 14 at post 20 as shown in FIG. 2a. The contraction of wire 38 causes the entire remaining portion of drive unit 24 to rotate against the spring 26. In other words, as wire 38 ohmicly heats due to the current supplied to it from coil 30 and its length contracts, wire 38 will cause shell 36 to rotate. Shell 36 is rotationally coupled or connected to ratchet 32, which rotates with shell 36 in both senses of rotation. Ratchet 32 is coupled to screw drive 34 through a conventional ratcheting mechanism (not shown) thereby causing screw drive 34 to rotate in one sense of rotation, but slipping with respect to screw drive 34 in the opposite sense of direction. Thus, the screw drive 34 is rotated within sleeve 16 and driven forward or to the left in FIG. 1 causing sleeve 14 to telescope out of sleeve 16. The combined length of sleeves 14 and 16 thus increases. When the wire 38 cools there is no further torque applied to shell 36 by wire 38, and torsion spring 26 will rotate shell 36 back to its original angular position within drive unit 24. Grooves are cut into the screw threads to resist rotation of screw drive 34 in the opposite direction thereby insuring that ratchet 32 slips against the screw drive 34 when shell 3 is returned to its original angular orientation. Screw drive 34 remains in a new advanced longitudinal position within sleeve 16. In this manner rod 10 can be repeatedly incrementally lengthened by repeated heat cycling of motor 28. Rod 10 can only lengthen and the ratcheting action of ratchet 32 prevents it from shortening. The ratchet 32 is designed to release or disengage from screw drive 34 when a screw-driver or Allen wrench is placed into through-hex socket 50 of screw drive 34 during surgical placement and adjustment. Torsion spring 26 also provides some longitudinal compressive force which tends to urge ratchet 32 against screw drive 34, but placement of a tool through socket 50 allows ratchet 32 to be backed off and to disengage from screw 32. Withdrawal of the tool then allows spring 26 to urge ratchet 32 back into engagement with screw drive 34. The initial length of rod 10 can thus be manually adjusted up or down at the time of its initial surgical implantation.

The pick-up coil 30 receives energy from an external hand-held source of energy (not shown), such as a low frequency generator of electromagnetic radiation, which is brought into proximity with coil 30. Rod 10 is implanted beneath the skin barrier, while the source of energy is exterior to the body. The external inductive power source may be driven at conventional line frequency. In the event that the coil 30 is be able to efficiently drive the muscle wire 38, then either a storage capacitor with a control diode can be added in circuit with coil 30, or with more complexity, a battery with a diode voltage multiplier, and control diode could be used. Any means of impedance matching between coil 30 and wire 38 on one hand and between coil 30 and the inductive power source on the other may be employed. The use of external power sources and inductively powered implanted coils is well known to the art and are routinely used, for example, in charging implanted pacemaker devices.

For a first alternative, energy would be fed into the pick-up coil until enough was stored in the capacitor to drive the motor 28. Upon the firing of the motor 28 the hand-held device would sense the discharge, and shut-off for the prescribed lock-out period.

The second alternative is the same, except that an on-board battery assists in charging the capacitor, and thus requires significantly more control electronics.

Figure 5:
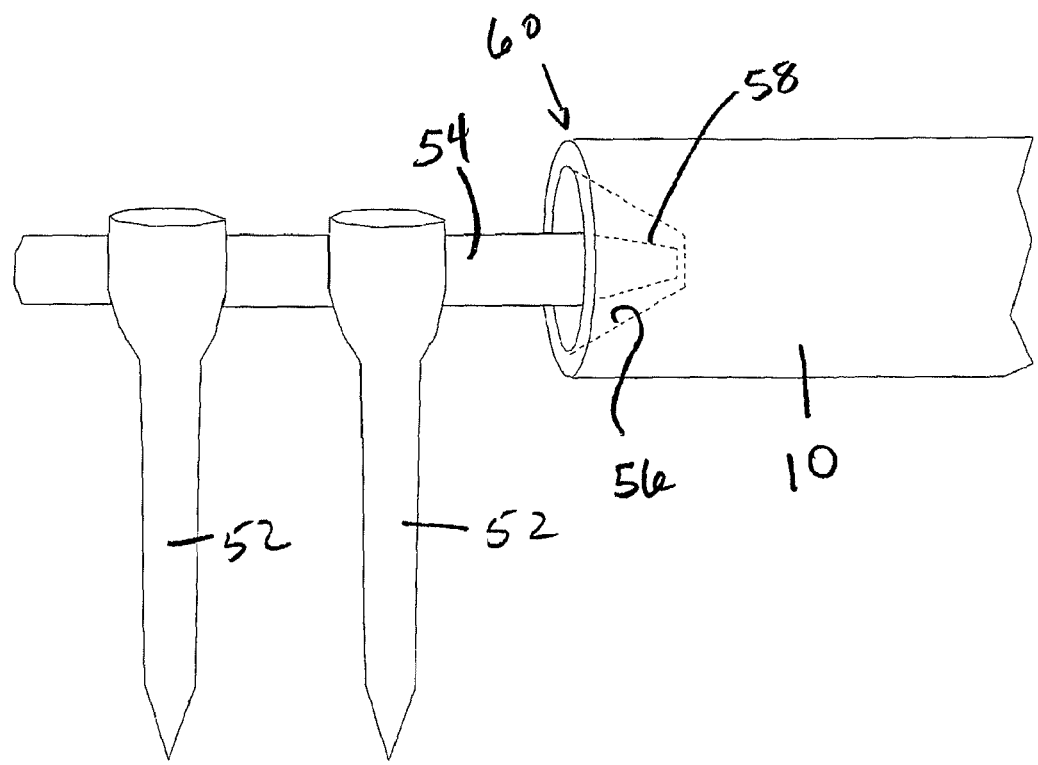
FIG. 5 is a side perspective view of a pair of pedicle screws showing a rotational coupling to the end of the rod of the invention.

Consider now the surgical implantation of rod 10 and its operation within the body. Two pedicle screws 52 as shown in FIG. 5 are placed at the top and two pedicle screws 52 at the bottom of the curve in a spine which being treated. Fixed head screws (not shown) are used. The expandable rod 10 is run above the fascia and beneath the skin between the two constructs. The rod 10 is then expanded daily typically for 2-3 months. The duration of treatment is variable and is determined according to medical considerations, which are not directly relevant here. After the desired curve in the spine is attained, the screws 52 and rod 10 are removed.

Figure 3:
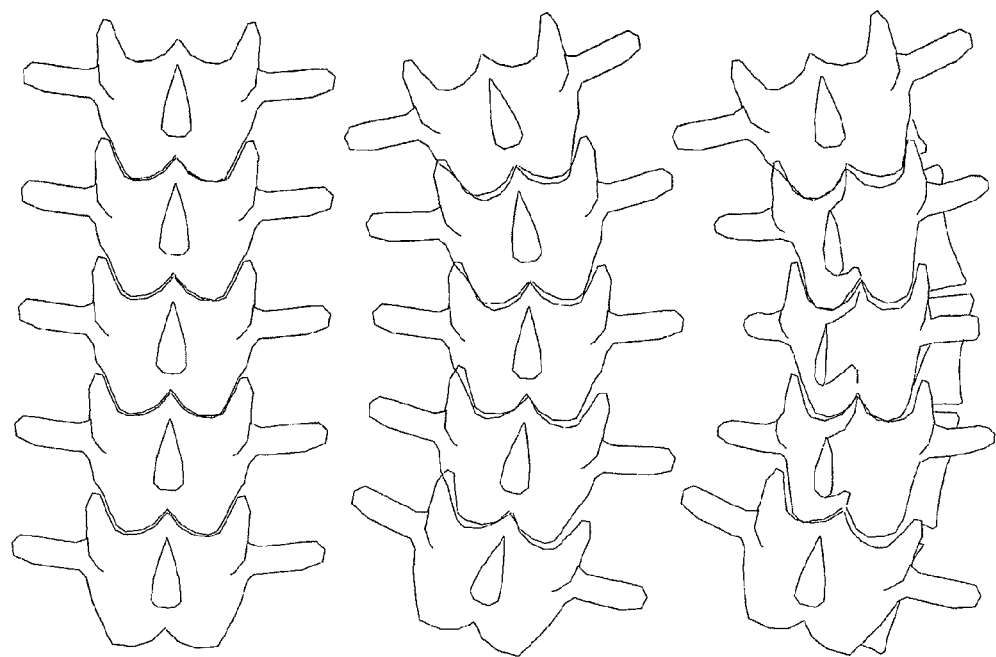
FIG. 3 is a posterior view, moving from the left to the right of the drawing, of a straight, lateral bending and sciolotic spine respectively.

FIG. 3 shows moving from left to right in the drawing a posterior view of a normal straight, normal in lateral bending, and a scoliotic spine. Note that with normal lateral bending as shown in the center there is no significant rotation. Indeed, in scoliosis as shown in the right most depiction as in lateral bending there is no significant increase in rotation. This is because scoliosis is caused by a tight ligamentum flavum. Because of this scoliosis patients have loss of kyphosis or are even lordotic, even in the thoracic spine. These facts can make a slight curve in the expanding rod 10 very useful as shown in the left most depiction in FIG. 4. As the spine straightens, rod 10 is also flexible enough to slowly straighten with the spine as shown in the right most depiction in FIG. 4.

Figure 4:
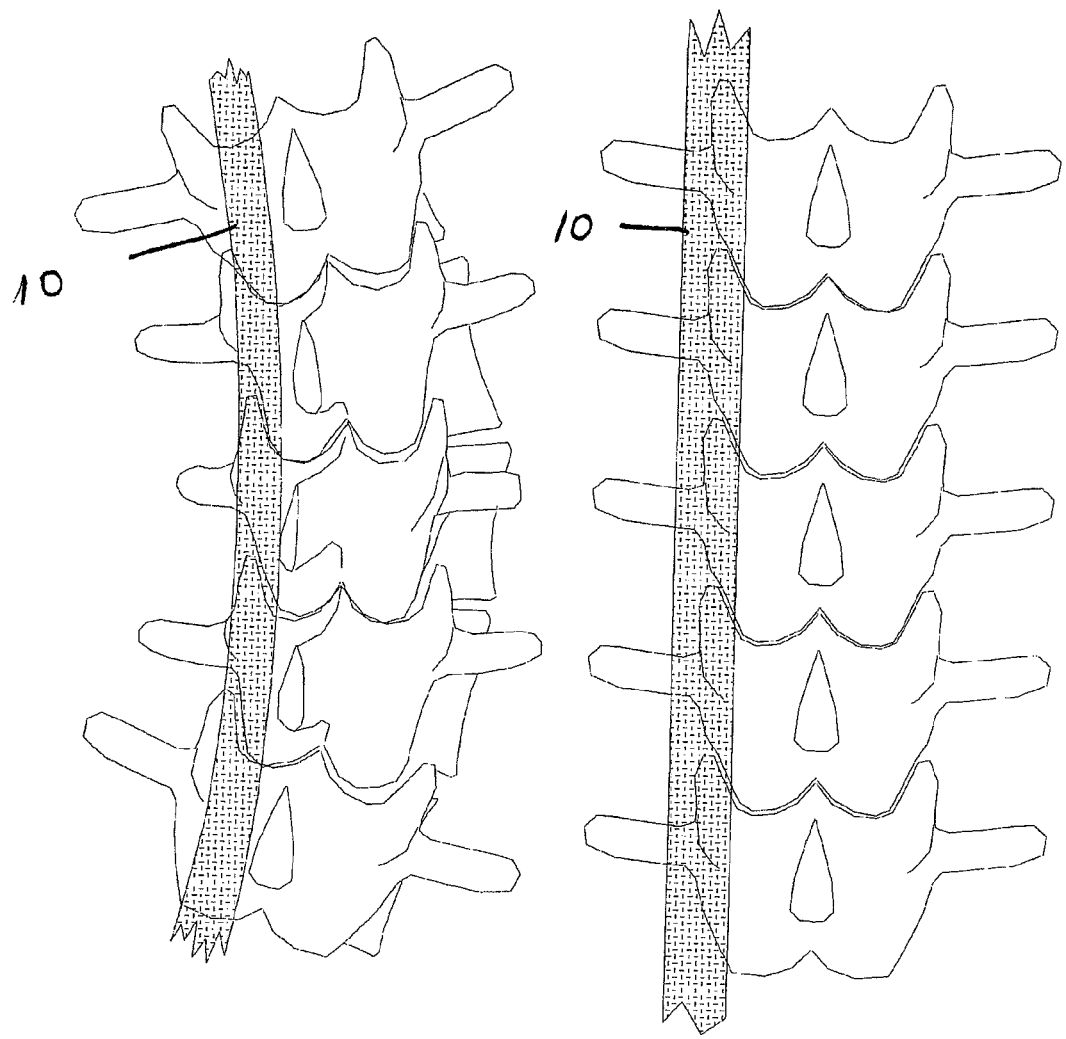
FIG. 4 is a posterior view of the rod of the invention as implanted next to a bent sciolotic spine in the left most depiction and next to a straightened spine in the right most depiction of the drawing.

FIG. 4 shows the initial rod placement in the left most drawing. As the rod 10 expands, the spine has nowhere to go except to have the pedicle screws 52 cut out or for the spine to straighten. Because the expansion is slow, the pedicle screws 52 don't cut out. As the spine straightens, and also because the rod 10 is posterior to the ligamentum flavum and is in a poor position to stretch the anterior longitudinal ligament, the spine will be pushed from a horizontal into a vertical position, thus restoring normal kyphosis.

In order to allow both rotation, and some play for the re-establishment of kyphosis, the rod-to-pedicle screw articulation is provided as shown in FIG. 5. Rod 10 is coupled to pedicle screws 52 by means of a pin 54 fixed to screws 52. The extend end 58 of pin 54 is tapered and is disposed into a conical socket 56 defined into the adjacent end 60 of rod 10. This allows rod 10 to swivel around the pivot provided between the socket-to-pin connection to rod 10 by fixed pin 54 and pedicle screws 52.

Scoliosis can be treated without difficult, conspicuous, (and ineffective) bracing; and without fusion. The key is to stretch out the ligamentum flavum. The proposed device discussed should be effective in stretching the spine out of scoliosis. This device would also have several applications other than the spine.

Many alterations and modifications may be made by those having ordinary skill in the art without departing from the spirit and scope of the invention. Therefore, it must be understood that the illustrated embodiment has been set forth only for the purposes of example and that it should not be taken as limiting the invention as defined by the following invention and its various embodiments.

For example, while a cycling rotational motor 28 with a rotary ratchet has been described, it is entirely within the scope of the invention that a cycled linear motor in combination with a linear ratcheting mechanism could be substituted to replace the illustrated embodiment.

Further, while an ohmicly heated motor is the preferred embodiment, it is also possible to conceive of use of a thermally or otherwise powered piston motor where the driving fluid may be heated by RF diathermy or ultrasound energy.

Still further the motor may be a rotary motor or linear motor with the propelling element of the motor is magnetically coupled to a moving magnetic field source and is combined through appropriate gearing to a ratcheting mechanism which telescopes rod 10.

Any means by which energy from an external source can be coupled into a motor which will mechanically telescope rod 10 is included within the spirit and scope of the invention.

Therefore, it must be understood that the illustrated embodiment has been set forth only for the purposes of example and that it should not be taken as limiting the invention as defined by the following claims. For example, notwithstanding the fact that the elements of a claim are set forth below in a certain combination, it must be expressly understood that the invention includes other combinations of fewer, more or different elements, which are disclosed in above even when not initially claimed in such combinations. A teaching that two elements are combined in a claimed combination is further to be understood as also allowing for a claimed combination in which the two elements are not combined with each other, but may be used alone or combined in other combinations. The excision of any disclosed element of the invention is explicitly contemplated as within the scope of the invention.

The words used in this specification to describe the invention and its various embodiments are to be understood not only in the sense of their commonly defined meanings, but to include by special definition in this specification structure, material or acts beyond the scope of the commonly defined meanings. Thus if an element can be understood in the context of this specification as including more than one meaning, then its use in a claim must be understood as being generic to all possible meanings supported by the specification and by the word itself.

The definitions of the words or elements of the following claims are, therefore, defined in this specification to include not only the combination of elements which are literally set forth, but all equivalent structure, material or acts for performing substantially the same function in substantially the same way to obtain substantially the same result. In this sense it is therefore contemplated that an equivalent substitution of two or more elements may be made for any one of the elements in the claims below or that a single element may be substituted for two or more elements in a claim. Although elements may be described above as acting in certain combinations and even initially claimed as such, it is to be expressly understood that one or more elements from a claimed combination can in some cases be excised from the combination and that the claimed combination may be directed to a subcombination or variation of a subcombination.

Insubstantial changes from the claimed subject matter as viewed by a person with ordinary skill in the art, now known or later devised, are expressly contemplated as being equivalently within the scope of the claims. Therefore, obvious substitutions now or later known to one with ordinary skill in the art are defined to be within the scope of the defined elements.

The claims are thus to be understood to include what is specifically illustrated and described above, what is conceptionally equivalent, what can be obviously substituted and also what essentially incorporates the essential idea of the invention.

I claim:

1. A method for treating scoliosis comprising:
  implanting an expandable telescoping rod subcutaneously within a subject, the expandable telescoping rod disposed on a posterior of the spine of the subject, wherein the expandable telescoping rod is in a curved state when it is secured to the spine, and wherein the expandable telescoping rod is in a curved state when it is secured to the spine, and wherein implantation comprises securing a first end of the expandable telescoping rod at a first location on the subject's spine and securing a second, opposing end of the expandable telescoping rod at a second location on the subject's spine, the expandable telescoping rod comprising a hollow outer sleeve and an inner sleeve coaxially disposed in the outer sleeve along a common longitudinal axis and wherein the hollow outer sleeve and inner sleeve are configured to limit rotational movement between the hollow outer sleeve and inner sleeve and wherein the hollow outer sleeve and inner sleeve are configured to limit rotational movement between the hollow outer sleeve and inner sleeve; and
  non-invasively applying an electromagnetic field from an external hand-held device to a drive unit disposed in the outer hollow sleeve to control the expansion of the expandable telescoping rod over an extended period of time until a desired spinal condition is obtained.

2. The method of claim 1, wherein at least one of the first and second ends of the expandable telescoping rod is secured to the spine via a rotational coupling.

3. The method of claim 2, wherein the rotational coupling comprises at least one pedicle screw.

4. The method of claim 1, wherein the expandable telescoping rod is implanted on a subject with adolescent scoliosis.

5. The method of claim 1, further comprising removing the expandable telescoping rod from the subject after the spinal condition is obtained.

6. The method of claim 1, wherein at least a posterior portion of the spine is stretched.

7. The method of claim 1, wherein at least a portion of the ligamentum flavum is stretched.

8. The method of claim 1, further comprising inserting a tool into the expandable telescoping rod during a shortening process.

9. The method of claim 1, wherein the expandable telescoping rod is expanded with a ratcheting movement.

10. The method of claim 1, wherein the drive unit comprises a rotatable propelling element.

11. The method of claim 1, wherein expansion of the expandable telescoping rod also results in rotation of the expandable telescoping rod about a pivot disposed at one or both of the first end and the second end.

12. The method of claim 1, wherein the external hand-held device is locked out for a period of time after actuation of the electromagnetic field from the external hand-held device.

13. The method of claim 1, wherein the telescoping rod is expanded over a period of less than 3 months.

14. The method of claim 1, wherein the telescoping rod has a diameter of ½ inch or less.

15. The method of claim 1, wherein the telescoping rod runs above the subject's fascia and beneath the subject's skin.

16. A method for treating scoliosis comprising:
  implanting an expandable telescoping rod subcutaneously within a subject, the expandable telescoping rod disposed on a posterior of the spine of the subject, wherein the expandable telescoping rod is in a curved state when it is secured to the spine, and wherein the expandable telescoping rod is in a curved state when it is secured to the spine, and wherein implantation comprises securing a first end of the expandable telescoping rod at a first location on the subject's spine and securing a second, opposing end of the expandable telescoping rod at a second location on the subject's spine, the expandable telescoping rod comprising a hollow outer sleeve and an inner sleeve coaxially disposed in the outer sleeve along a common longitudinal axis and wherein the hollow outer sleeve and inner sleeve are configured to limit rotational movement between the hollow outer sleeve and inner sleeve and wherein the hollow outer sleeve and inner sleeve are configured to limit rotational movement between the hollow outer sleeve and inner sleeve;

locating an external hand-held device near the subject;

conveying energy from the external hand-held device to an energy receiving element disposed on or in one of the outer hollow sleeve and inner sleeve; and converting the conveyed energy received by the energy receiving element to telescopic movement of the expandable telescoping rod.

17. The method of claim 16, wherein telescopic movement of the expandable telescoping rod also results in rotation of the expandable telescoping rod about a pivot disposed at one or both of the first end and the second end.

18. The method of claim 16, wherein the hand-held device is locked out for a period of time after actuation.

19. The method of claim 16, wherein the hand-held device conveys energy to the energy receiving element using a periodic signal.

20. The method of claim 16, wherein the telescoping rod has a diameter of ½ inch or less.

21. The method of claim 16, wherein the telescoping rod runs above the subject's fascia and beneath the subject's skin.

22. The method of claim 16, wherein the energy receiving element is disposed in the outer hollow sleeve.

23. The method of claim 16, wherein the expandable telescoping rod is implanted on a subject with adolescent scoliosis.

* * * * *

UNITED STATES PATENT AND TRADEMARK OFFICE
CERTIFICATE OF CORRECTION

PATENT NO. : 8,343,192 B2
APPLICATION NO. : 12/421569
DATED : January 1, 2013
INVENTOR(S) : Kiester It is certified that error appears in the above-identified patent and that said Letters Patent is hereby corrected as shown below:

Col. 8, Claim 1, Lines 10-12 remove "and wherein the expandable telescoping rod is in a curved state when it is secured to the spine,"

Col. 8, Claim 1, Lines 22-24 remove "and wherein the hollow outer sleeve and inner sleeve are configured to limit rotational movement between the hollow outer sleeve and inner sleeve"

Col. 8, Claim 1, Line 27 replace "outer hollow sleeve" with -- hollow outer sleeve --

Col. 9, Claim 16, Lines 3-5 remove "and wherein the expandable telescoping rod is in a curved state when it is secured to the spine,"

Col. 9, Claim 16, Lines 15-17 remove "and wherein the hollow outer sleeve and inner sleeve are configured to limit rotational movement between the hollow outer sleeve and inner sleeve"

Col. 9, Claim 16, Line 22 replace "outer hollow sleeve" with -- hollow outer sleeve --

Col. 10, Claim 22, Line 18 replace "outer hollow sleeve" with -- hollow outer sleeve --

Signed and Sealed this
Ninth Day of April, 2013

Teresa Stanek Rea
*Acting Director of the United States Patent and Trademark Office*